US009012476B2

(12) United States Patent
Zimmermann et al.

(10) Patent No.: US 9,012,476 B2
(45) Date of Patent: Apr. 21, 2015

(54) HYDROBROMIDE SALT OF PRIDOPIDINE

(71) Applicant: Teva Pharmaceutical Industries, Ltd., Petach-Tikva (IL)

(72) Inventors: Anne Zimmermann, København (DK); Brian Frøstrup, Lyngby (DK)

(73) Assignee: Ivax International GmbH, Rapperswil (CH)

( * ) Notice: Subject to any disclaimer, the term of this patent is extended or adjusted under 35 U.S.C. 154(b) by 0 days.

(21) Appl. No.: 13/708,816

(22) Filed: Dec. 7, 2012

(65) Prior Publication Data

US 2013/0150406 A1 Jun. 13, 2013

Related U.S. Application Data

(60) Provisional application No. 61/569,157, filed on Dec. 9, 2011.

(30) Foreign Application Priority Data

Dec. 8, 2011 (DK) ................................. 2011 70684

(51) Int. Cl.
*A01N 43/40* (2006.01)
*A61K 31/445* (2006.01)
*C07D 211/20* (2006.01)
*C07D 211/24* (2006.01)

(52) U.S. Cl.
CPC ..................................... *C07D 211/24* (2013.01)

(58) Field of Classification Search
None
See application file for complete search history.

(56) References Cited

U.S. PATENT DOCUMENTS

| | | | |
|---|---|---|---|
| 3,326,916 A | 6/1967 | Creighton et al. | |
| 3,539,573 A | 11/1970 | Schmutz et al. | |
| 4,048,314 A | 9/1977 | Kubela et al. | |
| 4,202,898 A | 5/1980 | Depoortere et al. | |
| 4,267,328 A | 5/1981 | Najer et al. | |
| 4,333,942 A | 6/1982 | Eistetter et al. | |
| 4,415,736 A | 11/1983 | Ciganek et al. | |
| 4,485,109 A | 11/1984 | Ciganek et al. | |
| 4,504,660 A | 3/1985 | Klaubert et al. | |
| 5,462,947 A | 10/1995 | Andersson | |
| 5,502,050 A | 3/1996 | Gross | |
| 6,121,259 A | 9/2000 | Yelle et al. | |
| 6,175,015 B1 | 1/2001 | Yuan et al. | |
| 6,903,120 B2 | 6/2005 | Sonesson et al. | |
| 6,924,374 B2 | 8/2005 | Sonesson et al. | |
| 7,417,043 B2 | 8/2008 | Sonesson et al. | |
| 7,923,459 B2 | 4/2011 | Gauthier et al. | |
| 2003/0100547 A1 | 5/2003 | Dwoskin et al. | |
| 2003/0109532 A1 | 6/2003 | Sonesson et al. | |
| 2006/0135531 A1* | 6/2006 | Sonesson et al. | 514/254.1 |
| 2007/0149542 A1 | 6/2007 | Sonesson | |
| 2007/0238879 A1* | 10/2007 | Gauthier et al. | 546/236 |
| 2008/0234321 A1 | 9/2008 | Sonesson | |
| 2009/0318500 A1 | 12/2009 | Trewartha et al. | |
| 2010/0076024 A1 | 3/2010 | Zimmermann et al. | |
| 2010/0105736 A1 | 4/2010 | Wikström | |
| 2013/0197031 A1 | 8/2013 | Sonesson | |
| 2013/0267552 A1 | 10/2013 | Waters et al. | |
| 2014/0088140 A1 | 3/2014 | Hayden et al. | |
| 2014/0088145 A1 | 3/2014 | Hayden et al. | |

FOREIGN PATENT DOCUMENTS

| | | |
|---|---|---|
| EP | 0060179 A1 | 9/1982 |
| EP | 0094159 A1 | 11/1983 |
| EP | 0369887 A2 | 5/1990 |
| EP | 0533266 A1 | 3/1993 |
| EP | 0533267 A1 | 3/1993 |
| EP | 0533268 A1 | 3/1993 |
| EP | 0675118 A2 | 10/1995 |
| EP | 0867183 | 9/1998 |
| EP | 1419773 A2 | 5/2004 |
| FR | 1459013 | 11/1966 |
| GB | 850662 | 10/1960 |
| GB | 1060160 | 4/1967 |
| GB | 2027703 | 7/1979 |
| GB | 1 560 271 | 2/1980 |
| GB | 2083476 A | 3/1982 |
| GB | 2078746 A | 1/1985 |
| NL | 6510107 | 2/1966 |
| WO | WO 89/05799 | 6/1989 |
| WO | WO 91/09594 | 7/1991 |
| WO | WO 92/18475 | 10/1992 |
| WO | WO 93/00313 | 1/1993 |
| WO | WO 93/04684 | 3/1993 |
| WO | WO 97/03986 | 2/1997 |
| WO | WO 98/11068 | 3/1998 |

(Continued)

OTHER PUBLICATIONS

MermaiHD Study by Neurosearch (results published Apr. 2010), http://neurosearch.com/Default.aspx?ID=8489.*
U.S. Appl. No. 13/820,024, filed Apr. 10, 2013, Sonesson.
Notification of Transmittal of the International Search Report and the Written Opinion of the International Searching Authority, or the Declaration, including an International Search Report and Written Opinion of the International Searching Authority, mailed Oct. 17, 2011 in connection with PCT International Application No. PCT/EP2011/064954, filed Aug. 31, 2011.
International Search Report and the Written Opinion of the International Searching Authority, or the Declaration, including an International Search Report and Written Opinion of the International Searching Authority, completed Mar. 21, 2002, in connection with PCT International Application No. PCT/SE00/02674, filed Dec. 22, 2000.

(Continued)

*Primary Examiner* — Craig Ricci
*Assistant Examiner* — Jared D Barsky
(74) *Attorney, Agent, or Firm* — John P. White; Gary J. Gershik; Cooper & Dunham LLP

(57) ABSTRACT

This invention relates to a new salt of Pridopidine, a drug substance currently in development for the treatment of Huntington's disease. More specifically the invention provides the pharmaceutically acceptable hydrobromide salt, pharmaceutical compositions comprising this salt, and uses of this salt as a drug substance.

17 Claims, 9 Drawing Sheets

(56) References Cited

FOREIGN PATENT DOCUMENTS

| WO | WO 00/03713 | 1/2000 |
|---|---|---|
| WO | WO 00/78728 | 12/2000 |
| WO | WO 01/46144 A1 | 6/2001 |
| WO | WO 01/46146 | 6/2001 |
| WO | WO 02/05819 | 1/2002 |
| WO | WO 02/59108 A1 | 1/2002 |
| WO | WO 03/064393 | 8/2003 |
| WO | WO 2004/099150 A1 | 11/2004 |
| WO | WO 2005/019215 | 3/2005 |
| WO | WO 2005/121087 | 12/2005 |
| WO | WO 2005/121088 | 12/2005 |
| WO | WO 2005/121092 A1 | 12/2005 |
| WO | WO 2006/039325 | 4/2006 |
| WO | WO 2006/040156 | 4/2006 |
| WO | WO 2007/023141 | 3/2007 |
| WO | WO 2007/042295 | 4/2007 |
| WO | WO 2007/065655 | 6/2007 |
| WO | WO 2007/128694 | 11/2007 |
| WO | WO 2011/014003 A2 | 2/2011 |
| WO | WO 2011/107583 A1 | 9/2011 |
| WO | WO 2011/107593 | 9/2011 |
| WO | WO 2013/034622 | 3/2013 |

OTHER PUBLICATIONS

International Preliminary Report on Patentability for PCT International Application No. PCT/EP05/011020 (WO 2006/040155) published Apr. 20, 2006 (Gauthier et al.).

Written Opinion of the International Search Authority for PCT International Application No. PCT/EP05/011020 (WO 2006/040155) published Apr. 20, 2006 (Gauthier et al.).

International Preliminary Report on Patentability and Written Opinion of the International Search Authority for PCT International Application No. PCT/SE2008/050414 (WO 2008/127188 A1), published Oct. 23, 2008 (Wikström).

European Search Report for European Patent Application No. 1419773 A2.

Citation of Prior Art under 37 C.F.R. §1.501, including Jul. 12, 2006 Korean Official Action.

Chemical Abstract CA 132:35590. "Synthesis of piperidine analogos of 1-(3-cholrophenyl)piperazine, a well known serotonin ligand." Radl et al., Journal of Heterocyclic Chemistry (1999). 36(4), pp. 1017-1022.

Chemical Abstract CA 116:250000. "Quantitative structure—metabolism relationship analyses of MAO-medicated toxication of 1-methyl-4-phenyl-1,2,3,5-tetrahydropyridine and analogs." Altomare et al., Chemical Research in Toxicology (1992), 5(3), pp. 366-375.

Carlsson et al., "Interactions Between Glutamatergic and Monoaminergic Systems within the Basal Ganglia—Implications for Schizophrenia and Parkinson's Disease", TINS, (1990), pp. 272-276, vol. 13, No. 7, Elsevier Science Publishers Ltd., United Kingdom.

Feldman et al. (Editors), "Principles of Neuropsychopharmacology", Chapter 17—Mind Altering Drugs, (1997), pp. 731, 762, 763, Sinauer Associates, Inc., Publishers, Sunderland, Massachusetts, USA.

Bloom et al. (Editors), "Psychopharmacology—The Fourth Generation of Progress", Chapter 21, pp. 227, 237, Chapter 22, pp. 245, 254, Chapter 25, pp. 283, 292, Chapter 26, pp. 295-301, Chapter 66, pp. 759-760, 1725, 744-746, Chapter 68, pp. 787, 793-795, Chapter 80, pp. 921-925, 927-928, Chapter 101, pp. 1205, 1207-1209, Chapter 111, pp. 1311, 1317, 1318, 1320, Chapter 126, pp. 1479-1482, Chapter 137, pp. 1591, 1600, Chapter 138, pp. 1609-1610, 1612, (1995), Raven Press, New York, New York, USA.

Grunblatt et al (PubMed Abstract 10335493) J Neural Transm Suppl. 1999; 55:57-70. "Potent neuroprotective and antioxidant activity of apomorphine in MPTP and 6-hydroxydopamine induced neurotoxicity,".

Coyle et al. Alzheimer's Disease: A Disorder of Cortical Cholinergic Innervation Science Mar. 11, 1983: 1184-1190.

Gesner et al., J Med Chem. Mar. 1985;28(3):311-7. "Synthesis and dihydropteridine reductase inhibitory effects of potential metabolites of the neurotoxin 1-methyl-4-phenyl-1,2,3,6-tetrahydropyridine."

Bergel et al., 1944, pp. 261 to 264. Beilstein Registry No. 183878 and 206256; Beilstein Institute for Organic Chemistry, Germany.

Nacci et al. "Antiblastic Substances. LII. Tylophorine Analogs. 1. Synthesis and Cytostotic and Cytoxic Activity of 3-(3,4-dimethoxyphenyl)piperidine", Farmaco, Edizone Scientifica, vol. 328, No. 5, 1973, pp. 399-419.

Chemical Abstract DN 65:38471 (also cited as NL 6510107, published Feb. 1966).

Zhang, et al., "Studies on antimalarials. III. Synthesis and antimalarial effects of some derivatives of 2,4-diamino-6-substituted piperazinylquinazolines", Acta Pharmaceutica Sinica, Jun. 1981, pp. 415-424, vol. 16, No. 6, Shanghai Inst. Pharm. Ind. Res., Shanghai, Peop, Rep. of China.

Takai, et al., "Reaction of Spiro[4H-3,1-benzoxazine-4,4'-piperdin]-2(1H)-one Derivatives and Related Compounds with Phosphorus Oxychloride", Chemical & Pharmaceutical Bulletin., May 1986, pp. 1901-1906, vol. 34, No. 5, Pharmaceutical Society of Japan, Tokyo, JP.

Egawa, et al., "A New Synthesis of 7H-Pyrido[1,2,3-de][1,4]benzoxazine Derivatives Including an Antibacterial Agent, Ofloxacin$_1$ ", Chemical & Pharmaceutical Bulletin, Oct. 1986, pp. 4098-4102, vol. 34, No. 10, Pharmaceutical Society of Japan, Tokyo, JP.

Beugelmans, et al., "Synthèsse d'hétérocycles à 5 et 6 chaînons par une stratégie combinant des réactions $S_N$ Ar et $S_{RN}1$", Bull Soc Chim Fr., 1995, pp. 306-313, vol. 132, Elsevier, Paris, FR.

Morita, et al., "Practical Application of the Palladium-catalyzed Amination in Phenylpiperazine Synthesis: An Efficient Synthesis of a Metabolite of the Antipsychotic Agent Aripiprazole", Tetrahedron, May 7, 1998, pp. 4811-4818, vol. 54, No. 19, Pergamon, Elsevier Science Ltd., Oxford, England & NY, USA.

Smaill, et al., "Mono- and difunctional nitrogen mustadr analougues of the DNA minor groove binder pibenzimol. Synthesis, cytotxicity and interaction with DNA", Anti-Cancer Drug Design, 1998, pp. 221-242, vol. 13, Oxford University Press.

Klaubert, et al., "N-(Aminophenyl)oxamic Acids and Esters a Potent, Orally Active Antiallergy Agent", J. Med. Chem., 1981, p. 742-748, vol. 24, American Chemical Society, Washington, DC.

Self, et al., "cine and tele Substitutions in the Reaction of 2,3-Dinitroaniline with Secondary Amines", J.C.S. Chem. Comm., 1980, pp. 281-282, Royal Society of Chemistry, UK.

Elslager, et al., "Folate Antagonists. 3. 2,4-Diamino-6-(heterocyclic)quinazolines, a Novel Class of Antimetabolites with Potent Antimalarial and Antibacterial Activity", Journal of Medicinal Chemistry, 1972, pp. 827-836, vol. 15, No. 8, American Chemical Society, Washington, DC.

Berberian, et al., "Comparison of Schistosomicidal Activity of Xanthenones and 4-Methyl-3-chloroanilines and Their Hydroxymethyl Analogs in Swiss Mice and Syrian Hamsters Infected with *Schistosoma mansoni*", Jpurnal of Medicinal Chemistry, Jul. 1969, pp. 607-610, vol. 12, No. 4, American Chemical Society, Washington, DC.

Henry, "A Facile Synthesis of Piperazines from Primary Amines (1)", Journal of Heterodyclic Chemistry, 1966, pp. 503-511, vol. 3, No. 4, Heterocorporation, USA.

Oshiro, et al., "Novel Antisychotic Agents with Dopamine Autoreceptor Agonist Properties: Synthesis and Pharmacology of 7-[4-(4-Phenyl-1-piperazinyl)butoxy]-3,4-dihydro-2(1H)-quinolinone Derivatives", J. Med. Chem., 1998, pp. 658-667, vol. 41, American Chemical Society, Washington, DC.

Manoury, et al., "Synthesis and Analgesic Activities of Some (4-Substituted phenyl-1-piperazinyl)alkyl 2-Aminobenzoates and 2-Aminocotinates", Journal of Medicinal Chemistry, 1979, pp. 554-559, vol. 22, No. 5, American Chemical Society, Washington, DC.

Strange, "Antipsychotic Drugs: Importance of Dopamine Receptors for Mechanisms of Therapeutic Actions and Side Effects", Pharmacologic Reviews, 2001, pp. 119-133, vol. 53, No. 1, The American Society for Pharmacology and Experimental Therapeutics, USA.

(56) References Cited

OTHER PUBLICATIONS

Sonesson et al., "Substituted (S)-Phenylpiperidines and Rigid Congeners as Preferential Dopamine Autoreceptor Antagonists: Synthesis and Structure-Activity Relationships"; Journal of Medicinal Chemistry, 1994 American Chemical Society; pp. 2735-2752.
Roth et al.; "Biochemical Pharmacology of Midbrain Dopamine Neurons"; Chapter 21; Yale University of Medicine; New Haven, CT; 1995. http://www.acnp.org/g4/GN401000021/Default.ht.
Moore et al., "Dopaminergic Neuronal Systems in the Hypothalamus"; Department of Pharmacology and Toxicology, Michigan State University, East Lansing,Michigan; Chapter 22; 1995. http://www.acnp.org/g4/GN401000022/CH.html.
Michel Le Moal, "Mesocorticolimbic Dopaminergic Neurons Functional and Regulatory Roles"; Universite de Bordeaux, Bordeaux, France; Chapter 25, 1995, http://www.acnp.org/g4/GN401000025/Default.htm.
Philip Seeman, "Dopamine Receptors Clinical Correlates"; Departmants of Pharmacology and Psychiatry, University of Toronto, Toronto, Ontario, Canada; Chapter 26, 1995. http://www.acnp.org/g4/GN401000027/Default.htm.
George F. Koon; "Animal Models of Drug Addiction"; Department of Neuropharmacology, The Scripps Research Institute, Lo Jolla, California, Chapter 66, 1995 http://www.acnp.org/g4/GN401000072/Default.htm.
Geyer et al., "Animal Models of Psychiatric Disorders"; Department of Neuropharmacology, The Scripps Research Institute, La Jolla, California; Chapter 68, 1995. http://www.acnp.org/g4/GN401000076/Default.htm.
Paul Willner; "Dopaminergic Mechanisms in Depression and Mania"; Department of Psychology, University College of Swansea, Wales, United Kingdom; Chapter 80; 1995 http://www.acnp.org/g4/GN401000093/Default.htm.
Bunney et al., "Schizophrenia and Glutamate"; Department of Pharmacology, University of Goteborg, Goteborg, Sweden; Chapter 101, 1995 http://www.acnp.org/g4/GN401000116/Default.htm.
Price et al., "Pharmacological Challenges in Anxiety Disorders"; University of Florida College of Medicine, Gainesville, Florida; Chapter 111; 1995 http://www.acnp.org/g4/GN401000126/Default.htm.
Amos D. Korczyn: "Parkinson's Disease", Tel Aviv University, Rama Aviv, Israel; Chapter 126; 1995 http://www.acnp.org/g4/GN401000142/Default.htm.
George A. Bray; "Obesity, Fat Intake, and Chronic Disease"; Pennington Biomedical Research Center, Louisiana State University, Baton Rouge, Louisiana; Chapter 137; 1995 http://www.acnp.org/g4/GN401000154/Default.htm.
Katherine A. Halmi; "Basic Biological Overview of Eating Disorders"; Cornell Medical Center—Westchester Division, White Plains, New York; Chapter 138; 1995 http://www.acnp.org/g4/GN401000155/Default.htm.
Sato et al., Oxidation of sulfides to sulfoxides and sulfones with 30% hydrogen peroxide under organic solvent—and halogen-free conditions; Department of Chemistry and Research Center for Materials Science; Nagoya University, Nagoya, Japan; pp. 2469-2476, 2001.
Rosenfeld et al., "Gas chromatographic method for analysis of Accession based on the Hofmann degradation reaction" STN Accession No. 1977:60610, Abstract of Journal of Chromatography (1976), 129.
Calligaro et al. "The synthesis and biological activity of some known and putative metabolites of the atypical antipsychotic agent olanzapine," Bioorganic and Medicinal Chemistry Letters, vol. 7, No. 1, Jan. 7, 1997, pp. 25-30(6).
Grundt et al. "Heterocyclic analogues of N-(4-(4-(2,3-dichlorophenyl)piperazin-1-yl)butyl)arylcarboxamides with functionalized linking chains as novel dopamine D3 receptor ligands: potential substance abuse therapeutic agents." J Med Chem. Aug. 23, 2007;50(17):4135-46. Epub Aug. 2, 2007.
Augst et al. "Prodrugs to Reduce Presystemic Metabolism" p. 340-355 (2007).
Bickel et al. "The Pharmacology and Biochemistry of N-Oxides" Pharm Rev. v.21(4) p. 325-355 (1969).
Dowald "Side Reaction in Organic Synthesis" p. ix (2005).
Kalgutkar et al. "Identification of an N-methyl-4-phenylpyridinium-like metabolite of the antidiarrheal agent loperamide in human liver microsomes: underlying reason(s) for the lack of neurotoxicity despite the bioactivation event,"Drug Meta. and Disposition v.32(9) p. 943-952 (2004).
Katritzky et al. "Conformational Analysis of Saturated Heterocycles" CA75:48309 (1971.
Rajsner et al. "Neurotropic and Psychotropic Agent" CA90:22967 (1979).
Sanner "Selective dopamine D4 receptor antagonists" Exp. Opino Ther. Patents vol. 8(4) p. 383-393 (1998).
Testa "Prodrugs : bridging pharmacodynamic/pharmacokinetic gaps" Curr. Opion. Chme. Biol.vol. 13 p. 338-344 (2009).
Apr. 23, 2004 Office Action in connection with U.S. Appl. No. 10/168,173.
Jul. 30, 2003 Office Action in connection with U.S. Appl. No. 10/168,173.
Dec. 7, 2005 Office Action in connection with U.S. Appl. No. 11/016,967.
Jun. 28, 2006 Office Action in connection with U.S. Appl. No. 11/016,967.
Aug. 9, 2007 Office Action in connection with U.S. Appl. No. 11/016,967.
Aug. 18, 2010 Office Action in connection with U.S. Appl. No. 11/733,512.
Nov. 17, 2009 Office Action in connection with U.S. Appl. No. 11/733,512.
Aug. 24, 2009 Office Action in connection with U.S. Appl. No. 11/733,512.
Mar. 12, 2009 Office Action in connection with U.S. Appl. No. 11/733,512.
Sep. 26, 2008 Office Action in connection with U.S. Appl. No. 11/733,512.
International Preliminary Report on Patentability for PCT International Application No. PCT/SE2008/050414 (WO 2008/127188 A1), published Oct. 23, 2008 (Wikström).
Written Opinion of the International Search Authority for PCT International Application No. PCT/SE2008/050414 (WO 2008/127188 A1), published Oct. 23, 2008 (Wikström).
Office Action issued Jun. 22, 2012 in connection with Australian Office Application No. 2008239841.
Office Action issued Dec. 3, 2012 in connection with European Patent Application No. 05793645.2.
Office Action issued Mar. 5, 2012 in connection with Indian Patent Application No. 3481/DELNP/2007.
Office Action issued Jul. 31, 2012 in connection with Israeli Patent Application No. 201401 (translation).
Office Action issued Apr. 28, 2003 in connection with European Patent Application No. 00 989162.3-2101.
Office Action issued Oct. 18, 2004 in connection with European Patent Application No. 00 989162.3-2101.
U.S. Appl. No. 14/342,253, Clas Sonesson et al.
U.S. Appl. No. 14/309,111, Merav Bassan et al.
Feb. 3, 2014 Opposition filed against Venezuelan Patent Application No. 001610-2012 by CIFAR.
Apr. 22, 2014 response to Feb. 3, 2014 Opposition filed against Venezuelan Patent Application No. 001610-2012 by CIFAR.
Apr. 23, 2012 Office Action in connection with U.S. Appl. No. 12/595,472.
Jul. 23, 2012 Response to Apr. 23, 2012 Office Action in connection with U.S. Appl. No. 12/595,472.
Sep. 18, 2012 Office Action in connection with U.S. Appl. No. 12/595,472.
Mar. 12, 2013 Response to Sep. 18, 2012 Office Action in connection with U.S. Appl. No. 12/595,472.
Apr. 4, 2014 Office Action in connection with U.S. Appl. No. 12/595,472.
Jul. 7, 2014 Response to Apr. 4, 2014 Office Action in connection with U.S. Appl. No. 12/595,472.

(56) References Cited

OTHER PUBLICATIONS

Aug. 14, 2014 Office Action issued in connection with U.S. Appl. No. 14/342,253.

Zimmermann et al. "Polymorphs of Pridopidine Hydrochloride" Cryst. Growth Des. 2012, 12, 2961-2968.

Notification Concerning Transmittal of Copy of International Preliminary Report on Patentability (Chapter I of the Patent Cooperation Treaty), including an International Preliminary Report on Patentability and Written Opinion of the International Searching Authority, mailed Mar. 20, 2014 by The International Bureau of WIPO in connection with PCT International Application No. PCT/EP2012/067371, filed Sep. 6, 2012.

Notification of Transmittal of the International. Search Report and the Written Opinion of the International Searching Authority, or the Declaration, including an International Search Report and Written Opinion of the International Searching Authority, mailed Feb. 22, 2013 in connection with PCT International Application No. PCT/US12/68582, filed Dec. 7, 2012.

"Biologic Test Methods", Burger's Medicinal Chemistry, Fourth Edition, Part III, Edited by Manfred E. Wolff, Apr. 1981, pp. 872-873, John Wiley & Sons, NY, USA.

* cited by examiner

HYDROBROMIDE SALT OF PRIDOPIDINE

This application claims priority of U.S. Provisional Application No. 61/569,157, filed Dec. 9, 2011 and Danish Patent Application No. PA 2011 70684, filed Dec. 8, 2011, the entire content of which are hereby incorporated by reference herein.

Throughout this application, various publications are referred to, and disclosures of these publications cited in their entireties are hereby incorporated by reference into this application in order to more fully describe the state of the art as of the date of the invention described herein.

TECHNICAL FIELD

This invention relates to a new salt of Pridopidine, a drug substance currently in development for the treatment of Huntington's disease. More specifically the invention provides the pharmaceutically acceptable hydrobromide salt, pharmaceutical compositions comprising this salt, and uses of this salt as a drug substance.

BACKGROUND ART

The crystal lattice of a pharmaceutical salt is composed of ionized drug molecules and counter ions of opposite charge, which form a unique crystal structure. Since the physicochemical properties of a drug is dictated by the crystal structure, different salt forms of a drug exhibit different physicochemical properties such as melting point, crystallinity and hygroscopicity—factors which can ultimately affect the processability, bioavailability, and stability of the drug. Therefore it is valuable to prepare and characterize various salt forms. Having different forms to choose from provides new opportunities to improve the performance of a pharmaceutical product.

Pridopidine, i.e. 4-(3-methanesulfonyl-phenyl)-1-propyl-piperidine, is a drug substance currently in clinical development for the treatment of Huntington's disease. The hydrochloride salt of 4-(3-methanesulfonyl-phenyl)-1-propyl-piperidine and a method for its synthesis is described in WO 01/46145. In WO 2006/040155 an alternative method for the synthesis of 4-(3-methanesulfonyl-phenyl)-1-propyl-piperidine is described. In WO 2008/127188 N-oxide and/or di-N-oxide derivatives of certain dopamine receptor stabilizers/modulators are reported, including the 4-(3-methanesulfonyl-phenyl)-1-propyl-piperidine-1-oxide.

DETAILED DISCLOSURE OF THE INVENTION

The present invention provides a pharmaceutically acceptable hydrobromide salt of Pridopidine.

Pridopidine is a weak base in the form of a tertiary amine with a calculated pKa value of 8.9.

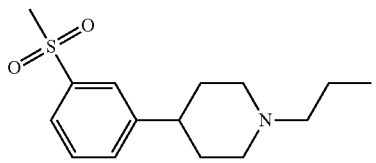 [SMILES: CCCN1CCC(c2cccc(S(C)(=O)=O)c2)CC1]

4-(3-methanesulfonyl-phenyl)-1-propyl-piperidine; Pridopidine

In its first aspect the invention provides a new crystalline form of 4-(3-methanesulfonyl-phenyl)-1-propyl-piperidine—a hydrobromide salt, or a solvate thereof.

In a preferred embodiment the crystalline hydrobromide is provided in an anhydrous form.

In another preferred embodiment the crystalline hydrobromide is provided in an anhydrous form and non-solvated form.

The crystalline hydrobromide of the invention is characterised by a powder X-ray diffractogram having the d-spacing's shown in Table 1 below, or a diffractogram substantially as depicted in FIG. 1.

TABLE 1

| d-spacing's |
| d-spacing's, Pridopidine hydrobromide |

| 7.6 | 6.9 | 6.0 | 5.4 | 5.3 | 4.3 | 4.2 | 4.0 | 3.8 | 3.6 | 3.1 |
|---|---|---|---|---|---|---|---|---|---|---|

Therefore, in a third preferred embodiment, the crystalline 4-(3-methanesulfonyl-phenyl)-1-propyl-piperidine hydrobromide salt of the invention is characterized by having an X-ray powder diffraction pattern with reflections corresponding to the d-spacing values 6.0 and 3.8.

In a more preferred embodiment, the crystalline hydrobromide of the invention is characterized by having an X-ray powder diffraction pattern with reflections corresponding to the d-spacing values 3.6 and 4.0.

In another more preferred embodiment, the crystalline hydrobromide of the invention may be characterized by having an X-ray powder diffraction pattern with reflections corresponding to the d-spacing values 7.6, 6.9, 6.0, 5.4, 4.3, 4.2, 4.0, 3.8, 3.6, 3.1.

In a fourth preferred embodiment, the crystalline hydrobromide of the invention may be characterized by having a DSC thermogram substantially as shown in FIG. 2.

In a fifth preferred embodiment, the crystalline hydrobromide of the invention may be characterized by having an endotherm with an onset of about 196° C., as obtained with DSC.

In a sixth preferred embodiment, the crystalline hydrobromide of the invention may be characterized by having an IR spectrum substantially as depicted in FIG. 3.

In a seventh preferred embodiment, the crystalline hydrobromide of the invention may be characterized by having a TGA thermogram substantially as depicted in FIG. 4.

The hydrobromide crystallises in the orthorhombic space group $P2_12_12_1$ with the lattice parameters a=7.3170(10)Å, b=10.7189(15)Å, c=21.880(3)Å, α=90° C., β=90° C., γ=90° C., and cell volume 1716.05 Å$^3$.

The dynamic vapour sorption (DVS) profile shows that the hydrobromide is non-hygroscopic and non-deliquescent as the salt has gained less than 1% weight at the 95% relative humidity (RH) level, see FIG. 5. Therefore, in an eighth preferred embodiment, the crystalline hydrobromide of the invention may be characterized by having a DVS profile substantially as depicted in FIG. 5.

TGA shows the hydrobromide to be a non-solvated form (see FIG. 4), and Karl Fisher analysis confirmed the anhydrous nature of the salt.

One of the many steps in the drug development process is identifying a solid form of the drug which can serve as an effective drug product. The formulation must be effective at delivering the active molecule to the targeted bio system. Newman and Stahly, "Form Selection of Pharmaceutical Compounds," in Handbook of Pharmaceutical Analysis, 18, 18 (2002). Reaction of bioactive organic molecules with acids or bases produce salts, which have different physical properties than the base compound. One important property of a Drug substance is its hygroscopicity. Newman and Stahly, "Form Selection of Pharmaceutical Compounds," in Handbook of Pharmaceutical Analysis, 18, 19 (2002).

The physical properties of a hydrobromide salt of a compound, such as hygroscopicity, cannot be predicted. The literature has several examples of hydrobromide salts, however, the salt is sometimes hygroscopic and sometimes non-hygroscopic. For instance, the hydrobromide salt in US Patent Publication No. 2012/0053195, and U.S. Pat. No. 6,110,940 are non-hygroscopic. In comparison, the hydrobromide salt in Parenty et al., "General one-pot, three-step methodology leading to an extended class of N-heterocyclic cations: spontaneous nucleophilic addition, cyclization, and hydride loss." J. Org. Chem. 69(18):5934-5946 (2004) is hygroscopic.

Hydrochloride Salt of Pridopidine

The hydrochloride salt of pridopidine disclosed in WO 01/46145 is non-hygroscopic at relative humidities below 86%, but deliquescent in excess of 86% relative humidity. This means that the salt is able to take up so much moisture from the surroundings that the salt is dissolved. The claimed invention retains the same therapeutic properties as the hydrochloride salt previously disclosed, yet is non-hygroscopic up to at least 95% relative humidity.

Experimental Data for the Hydrochloride Salt of Pridopidine

Three batches of the hydrochloride (HCl) salt of pridopidine, made with GMP (good manufacturing practice), were examined. DVS analysis was performed on two of the HCl salts of pridopidine (HCl salt of pridopidine batches A and B). A full two cycle sorption and desorption profile was obtained for a third HCl salt of pridopidine (hydrochloride salt of pridopidine batch C). Moisture sorption kinetics in the first sorption cycle is rather fast. At the 90% relative humidity step and onward, sorption and desorption kinetics are substantially slower (see FIG. 7). At 90% relative humidity, large amounts of moisture are adsorbed and weight gain of approximately 80% was observed. The following desorption and adsorption cycles shows almost identical behaviour, but are substantially different from the first sorption cycle. This indicates a change to the solid phase of the material (See FIG. 7 and FIG. 8).

An additional run was performed in the mid-eighties relative humidity range in order to indentify the transition point in more detail. (See FIG. 9). For this the hydrochloride salt of pridopidine batch B was used, however a single cycle DVS run of hydrochloride salt of pridopidine batch B showed the same moisture sorption properties as hydrochloride salt of pridopidine batch A. At the end of the cycle, it was observed that the specimen had completely dissolved. This shows that the hydrochloride salt of pridopidine is deliquescent in excess of 86% relative humidity.

The Pridopidine Hydrobromide Salt

Methods of Preparation

The 4-(3-methanesulfonyl-phenyl)-1-propyl-piperidine hydrobromide salt of the invention may be prepared by conventional methods for salt formation and crystallization, e.g. as described in the working example.

Experimental Data

DVS analysis was performed on the HBr salt and the results are shown in FIG. 5 and FIG. 6. Between 0 and 95% RH the salt gradually gained approximately 0.15% weight, which was lost again during desorption. Sorption and desorption kinetics were rapid as two full cycles were performed in 225 minutes. In the 90% desorption step a combined desorption and adsorption was observed (FIG. 6).

The origin of this observation has yet to be investigated. The profile was more or less repeatable between cycles, however a slight hysteresis was observed. Thus, the result indicates that the NS30016-HBr salt is non-hygroscopic.

Biological Activity

WO 01/46145, WO 01/46146, WO 2005/121087, WO 2007/042295 WO 2008/127188 and WO 2008/155357 all describe substituted 4-phenyl-N-alkyl-piperazines and 4-phenyl-N-alkyl-piperidines, reported to be modulators of dopamine neurotransmission, and to be useful in treatment of symptoms of various disorders of the central nervous system. The 4-(3-methanesulfonyl-phenyl)-1-propyl-piperidine hydrobromide salt of the invention is considered useful for the same medical indications as described in these publications, and these publications therefore are incorporated by reference.

Neurological indications contemplated according to these publications include the treatment of Huntington's disease and other movement disorders, as well as movement disorders induced by drugs. Therefore, in a preferred embodiment, the invention relates to the use of the 4-(3-methanesulfonyl-phenyl)-1-propyl-piperidine hydrobromide salt of the invention for use as a medicament for the treatment of Huntington's disease.

Other indications contemplated according to these publications are treatment of neurologic and psychiatric disorders, such as Parkinson's disease and schizophrenia; disorders related to ageing, for preventing bradykinesia and depression and for the improvement of mental functions. The claimed compounds may also be used to improve cognitive functions and related emotional disturbances in neurodegenerative and developmental disorders as well as after brain damage.

The compounds according to the invention can be used to improve symptoms of psychosis, including schizo-phrenia and schizophreniform disorders as well as drug induced psychotic disorders. The compounds according to the invention may also be used in behavioral disorders usually first diagnosed in infancy, childhood, or adolescence as well as in impulse control disorders. Also, speech disorders such as stuttering may improve. Other psychotic disorders not characterized as schizophrenia, schizoaffective syndromes as well as psychotic symptoms, delusions and hallucinations induced by other drugs may also improve. Disruptive behavior disorders such as attention deficit hyperactivity disorder (ADHD), conduct disorder and oppositional defiant disorder may also improve. They can also be used in tic disorders such as Gilles de la Tourette's syndrome and other tic disorders. Also, speech disorders such as stuttering may improve. They may also be used for treating substance abuse disorders as well as disorders characterized by misuse of food.

Mood and anxiety disorders, personality disorders, and conversion hysteria may also be treated with the compounds according to the invention.

Neurological indications include the treatment of Huntington's disease and other movement disorders as well as movement disorders induced by drugs. Restless legs and related disorders as well as narcolepsy may also be treated with compounds included according to the invention. They may also improve mental and motor function in Parkinson's disease, and in related parkinsonian syndromes. They may also be used to ameliorate tremor of different origins. They may be used in the treatment of headaches and used to improve brain function following vascular or traumatic brain injury. Moreover, they may be used to relieve pain in conditions characterized by increased muscle tone.

The compounds according to the present invention have been found to act specifically on dopaminergic systems in the brain. They have effects on bio-chemical indices in the brain with the characteristic features of selective dopamine antagonists, e.g. producing increases in concentrations of dopamine metabolites.

The compounds according to the invention are especially suitable for treatment of disorders in the central nervous system, and particularly for treatment of dopamine mediated disorders. They may, e.g. be used to amelio-rate symptoms of mood disorders, in obesitas as an an-orectic agent and in other eating disorders, to improve cognitive functions and related emotional disturbances, to improve cognitive and motor dysfunctions associated with developmental disorders, to improve symptoms of schizophrenia and schizophreniform disorders as well as other psychoses, to improve ongoing symptoms as well as to prevent the occurrence of new psychotic episodes, to regulate pathological disorders due to intake of food, coffee, tea, tobacco, alcohol, addictive drugs etc.

The compounds according to the invention can thus be used to treat symptoms in e.g.:

Neurological indications include the treatment of Huntington's disease, movement disorders such as dyskinesias including other choreas as well as primary, secondary and paroxysmal dystonias, tardive movement disorders such as tardive dyskinesia and tardive dystonia as well as other drug induced movement disorders. Restless legs, periodic leg movements and narcolepsy may also be treated with compounds included in the invention. They may also improve mental and motor function in Parkinson's disease, and in related parkinsonian syndromes such as multiple system atrophies, progressive supranuclear palsy, diffuse Lewy body disorder and vascular parkinsonism. They may also be used to ameliorate tremor of different origins. The compounds in the invention can also be used for the treatment of vascular headaches such as migraine and cluster headache, both as acute and prophylactic treatment. They may improve rehabilitation following vascular or traumatic brain injury. Moreover, they may be used to relieve pain in conditions characterized by increased muscle tone.

schizophrenia and other psychotic disorders, such as catatonic, disorganized, paranoid, residual or differentiated schizophrenia; schizophreniform disorder; schizo-affective disorder; delusional disorder; brief psychotic disorder; shared psychotic disorder; psychotic disorder due to a general medical condition with delusions and/or hallucinations;

mood disorders, such as depressive disorders, e.g., dysthymic disorder or major depressive disorder; bipolar disorders, e.g., bipolar I disorder, bipolar II disorder, and cyclothymic disorder; mood disorder due to a general medical condition with depressive, and/or manic features; and substance-induced mood disorder;

anxiety disorders, such as acute stress disorder, agoraphobia without history of panic disorder, anxiety disorder due to general medical condition, generalized anxiety disorder, obsessive-compulsive disorder, panic disorder with agoraphobia, panic disorder without agoraphobia, posttraumatic stress disorder, specific phobia, social phobia, and substance-induced anxiety disorder;

eating disorders, such as anorexia nervosa, bulimia nervosa, and obesitas;

sleep disorders, such as dyssomnias, e.g., breathing-related sleep disorder, circadian rhythm sleep disorder, hypersomnia, insomnia, narcolepsy, "jet lag" and disorders of sexual functions;

impulse-control disorders not elsewhere classified, such as intermittent explosive disorder, kleptomania, pathological gambling, pyromania, and trichotillomania;

personality disorders, such as paranoid, schizoid or schizotypal disorder; antisocial, borderline, histrionic, and narcissistic disorder; and avoidant, dependent, obsessive-compulsive disorder;

medication-induced movement disorders, such as neuroleptic induced parkinsonism, neuroleptic malignant syndrome, neuroleptic induced acute and tardive dystonia, neuroleptic induced akathisia, neuroleptic induced tar-dive dyskinesia, medication induced tremor, and medication induced dyskinesias;

substance-related disorders, such as abuse, dependence, anxiety disorder, intoxication, intoxication delirium, psychotic disorder, psychotic disorder with delusions, mood disorder, persisting amnestic disorder, persisting dementia, persisting perception disorder, sexual dysfunction, sleep disorder, withdrawal, and withdrawal delirium due to use ore misuse of alcohol, amphetamine (or amphetamine-like substances), caffeine, cannabis, cocaine, hallucinogens, inhalants, nicotine, opioids, phencycli-dine (or phencyclidine-like substances), sedative substances, hypnotic substances, and/or anxiolytic substances;

disorders usually first diagnosed in infancy, child-hood, or adolescence, such as mental retardation; learning disorders; motor skills disorders, e.g. developmental coordination disorder; communication disorders, e.g. expressive language disorder, phonological disorder, receptive-expressive language disorder and stuttering; pervasive developmental disorders, e.g. Asperger's disorder, autistic disorder, childhood disintegrative disorder, and Rett's disorder; attention-deficit and disruptive behavior disorders, e.g. attention-deficit/hyperactivity disorder, conduct disorder, and op-positional defiant disorder; feeding and eating disorders of infancy or early childhood, e.g. feeding disorder of infancy or early childhood, pica, rumination disorder; tic disorders, e.g. chronic motor or vocal tic disorder, and Tourette's disorder; other disorders of infancy, childhood, or adolescence, e.g. selective mutism, and stereotypic movement disorder;

delirium, dementia, amnestic and other cognitive disorders, such as Alzheimer's, Creutzfeldt-Jakob disease, dead trauma, Huntington's disease, HIV disease, Pick's disease, and diffuse Lewy body dementia;

conversion hysteria;

conditions connected to normal aging, such as disturbances in motor functions and mental functions;

Parkinson's Disease and related disorders, such as multiple system atrophies, e.g. striatonigral degeneration, olivopontocerebellar atrophy, and shydrager syndrome; progressive supranuclear palsy; corticobasal degeneration; and vascular parkinsonism;

tremors, such as essential, orthostatic, rest, cerebel-lar, and secondary tremor headaches, such as migraine, cluster headache, tension type headache, and paroxysmal headache;

movement disorders, such as dyskinesias, e.g. in deneral medicine condition, secondary to trauma or vascular insult, hemiballism, athetosis, Sydenham's chorea, and paroxysmal; dystonias; Ekbom's syndrome (restless legs); Wilson's Disease; Hallerworden-Spatz disease;

rehabilitation medicine, e.g. to improve rehabilitation after vascular or traumatic brain injury;

Movement disorders induced by drugs

Parkinson's disease in early stages, before introducing L-dopa or directly acting dopamine receptor agonists, or together with low doses of the same. Restless legs, again either monotherapy or combinations. Mental fatigue, associated with high age, stroke, and postencephalitic. Autism spectrum disorders. Lapses of consciousness, e.g. narcolepsy and petit mal epilepsy, syncope. Sleeping disorders, e.g. hypersomnia, sleep apnea, attacks of sleep induced e.g. by dopamine receptor agonists. Emesis and nausea, induced by dopamine agonists, other drugs, motion sickness and other causes. Dopamine hypofuction induced by antipsychotic drugs, e.g. ex-trapyramidal symptoms, depression, loss of initiative, cognitive deficits (combined treatment).

pain in conditions characterized by increased muscular tone, such as fibromyalgia, myofascial syndrome, dysto-nia, and parkinsonism; as well as conditions related to the above that fall within the larger categories but does not meet the criteria of any specific disorder within those categories.

Pharmaceutical Compositions

Viewed from another aspect the invention provides 4-(3-methanesulfonyl-phenyl)-1-propyl-piperidine hydrobromide salt, or a solvate thereof, in a crystalline form, for use as medicaments. Therefore, in another aspect, the invention provides novel pharmaceutical compositions comprising a therapeutically effective amount of the compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

Pharmaceutical compositions of the invention may in particular be formulated as described in WO 01/46145.

Further details on techniques for formulation and administration may be found in the latest edition of *Remington's Pharmaceutical Sciences* (Maack Publishing Co., Easton, Pa.).

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 1 to about 500 mg of active ingredient per individual dose, preferably of from about 10 to about 150 mg, most preferred of from about 25 to about 50 mg, are suitable for therapeutic treatments. The daily dose will preferably be administered in individual dosages 1 to 4 times daily. In another preferred embodiment, the dose of the active ingredient will be 45 mg and be administered two times per day. In another preferred embodiment, the dose of the active ingredient will be 67.5 mg administered two times per day.

Drug Formulations

General techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

The claimed hydrobromide salt of pridopidine may contain any of the following non-toxic auxiliary substances:

The multiplicity of configurations may contain additional beneficial biologically active agents which further promote tissue health. The claimed hydrobromide salt of pridopidine may also contain antibacterial agents which are non-injurious in use, for example, thimerosal, benzalkonium chloride, methyl and propyl paraben, benzyldodecinium bromide, benzyl alcohol, or phenylethanol.

The claimed hydrobromide salt of pridopidine disclosed herein can also comprise excipients such as solubility-altering agents (e.g., ethanol, propylene glycol and sucrose) and polymers (e.g., polycaprylactones and PLGA's) as well as pharmaceutically active compounds.

The claimed hydrobromide salt of pridopidine may also contain buffering ingredients such as sodium acetate, gluconate buffers, phosphates, bicarbonate, citrate, borate, ACES, BES, BICINE, BIS-Tris, BIS-Tris Propane, HEPES, HEPPS, imidazole, MES, MOPS, PIPES, TAPS, TES, and Tricine.

The claimed hydrobromide salt of pridopidine may also contain a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, peanut oil, polyalkylene glycols, petroleum based jelly, ethyl cellulose, ethyl oleate, carboxymethyl-cellulose, polyvinylpyrrolidone, isopropyl myristate and other conventionally employed acceptable carriers.

The claimed hydrobromide salt of pridopidine may also contain non-toxic emulsifying, preserving, wetting agents, bodying agents, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic.

The claimed hydrobromide salt of pridopidine may also contain surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold, for example, by BASF under the trademark Cremaphor.

The claimed hydrobromide salt of pridopidine may also contain wetting agents commonly used in ophthalmic solutions such as carboxymethylcellulose, hydroxypropyl methylcellulose, glycerin, mannitol, polyvinyl alcohol or hydroxyethylcellulose and the diluting agent may be water, distilled water, sterile water, or artificial tears, wherein the wetting agent is present in an amount of about 0.001% to about 10%.

The formulation of this invention may be varied to include acids and bases to adjust the pH; tonicity imparting agents such as sorbitol, glycerin and dextrose; other viscosity imparting agents such as sodium carboxymethylcellulose, microcrystalline cellulose, polyvinylpyrrolidone, polyvinyl alcohol and other gums; suitable absorption enhancers, such as surfactants, bile acids; stabilizing agents such as antioxidants, like bisulfites and ascorbates; metal chelating agents, such as sodium edetate; and drug solubility enhancers, such as polyethylene glycols. These additional ingredients help make commercial solutions with adequate stability so that they need not be compounded on demand.

Other materials as well as processing techniques and the like are set forth in Part 8 of Remington's Pharmaceutical Sciences, 17th edition, 1985, Mack Publishing Company, Easton, Pa., and International Programme on Chemical Safety (IPCS), which is incorporated herein by reference.

Methods of Therapy

In another aspect the invention provides a method for the treatment, prevention or alleviation of a dopamine mediated disorder of a living animal body, including a human, which method comprises the step of administering to such a living animal body in need thereof a therapeutically effective amount of the 4-(3-methanesulfonyl-phenyl)-1-propyl-piperidine hydrobromide salt of the invention.

In a preferred embodiment the dopamine mediated disorder is Huntington's disease.

BRIEF DESCRIPTION OF THE DRAWINGS

The present invention is further illustrated by reference to the accompanying drawing, in which.

EXAMPLE 1

Preparation of Pridopidine HBr

In order to prepare 33 g of pridopidine HBr, 28.5 g of free base was dissolved in 150 ml 99% ethanol at room temperature. 1.5 equivalents of hydrobromic acid 48% were added. Precipitation occurred spontaneously, and the suspension was left in refrigerator for 2.5 hours. Then the crystals were filtered, followed by washing with 99% ethanol and ether. The crystals were dried over night under vacuum at 40° C.: m.p. 196° C. The results of a CHN analysis are presented in Table 2, below.

NMR $^1$H NMR (DMSO-$d_6$): 0.93 (3H, t), 1.68-1.80 (2H, m), 1.99-2.10 (4H, m) 2.97-3.14 (5H, m), 3.24 (3H, s), 3.57-3.65 (2H, d), 7.60-7.68 (2H, m), 7.78-7.86 (2H, m) and 9.41 ppm (1H, bs).

TABLE 2

| Elemental analysis | | | |
|---|---|---|---|
| | Result W/W % (n = 2) Element | | |
| Elemental analysis | C | H | N |
| Theoretical content Anhydrous Pridopidine HBr | 49.72 | 6.68 | 3.87 |
| Measured | 49.95 | 6.66 | 3.81 |

Example

Analytical Methods

X-Ray Powder Diffraction

X-ray powder diffraction (XRPD) experiments were conducted using a Bruker D8 Advance diffractometer configured as listed below:

| | |
|---|---|
| Goniometer | Theta-theta |
| Geometry | Bragg-Brentano geometry |
| Primary slit | 1.0 mm and 2.5° soller slit |
| Secondary collimator | 1.0 mm and 2.5° Soller slit |
| Detector slit | 0.1 mm |
| Monochromator | Ni-filter |

| | |
|---|---|
| Detector | Scintillation counter |
| Scan range | 3-30°, 2 Theta |
| Scan speed | 5 s/step, 0.020° 2 theta/step |
| Radiation | CuK$_\alpha$ ($\lambda$ = 1.5418) |
| Generator | 40 kV, 40 mA |
| Sample stage | 9 position, spinning mode |

The sample was placed on a zero back ground silicon single crystal sample holder in a thin film of vaseline. The diffractograms were acquired using Bruker "XRD Commander", ver. 2.6.1, and was evaluated using "Bruker Evaluation", ver. 11,0,0,3.

Figure 1:
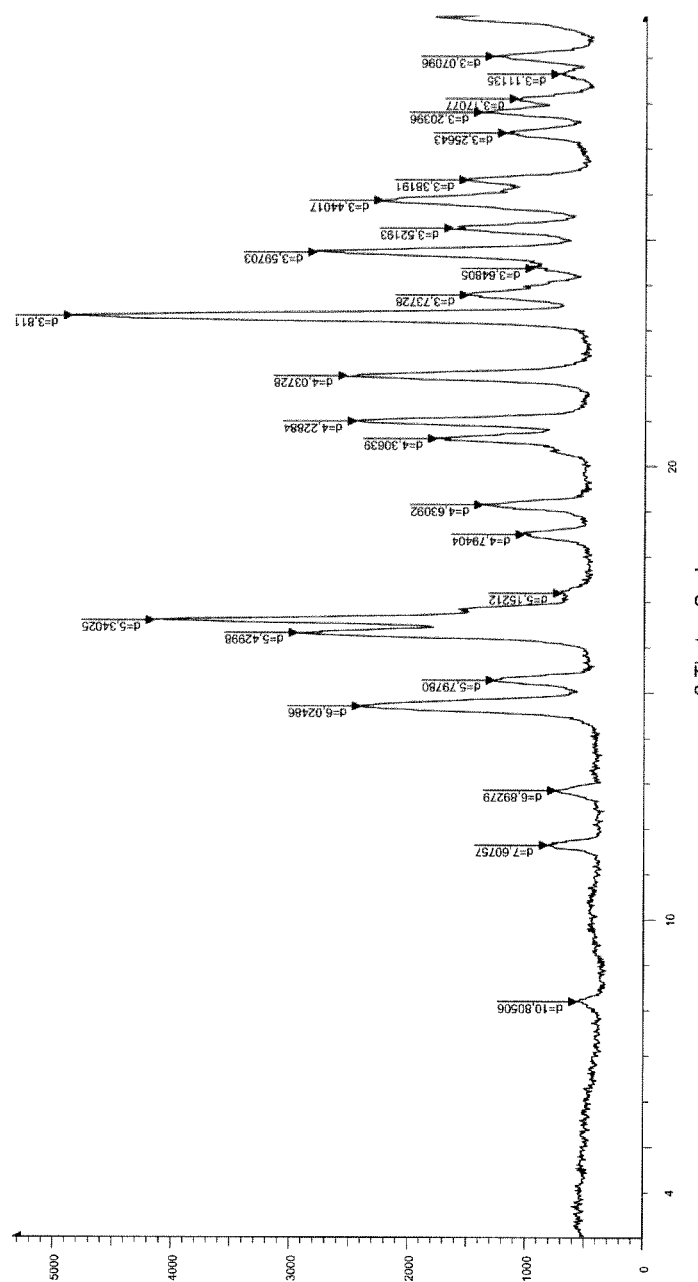
FIG. 1 shows a characteristic X-ray powder diffraction pattern of crystalline Pridopidine hydrobromide.

Following this procedure the d-spacing's shown in Table 1, and the diffractogram shown in FIG. 1, were obtained. FIG. 1 has an X-ray powder diffraction pattern with reflections corresponding to the following d-spacing values: 10.8, 7.6, 6.9, 6.0, 5.7, 5.4, 5.3, 5.2, 4.7, 4.6, 4.3, 4.2, 4.0, 3.8, 3.7, 3.6, 3.5, 3.4, 3.3, 3.2, 3.1.

Differential Scanning Calorimetry

Differential scanning calorimetry (DSC) experiments were conducted on a Mettler Toledo DSC 821e Differential Scanning Calorimeter, using Mettler-Toledo StarE ver. 9.2 software package. The sample (approx. 3 mg) was heated in a pinholed aluminium pan from 30° C. to 300° C. at 10° C./min. The DSC was continuously purged with dry nitrogen, and was routinely calibrated with indium and zinc.

Figure 2:
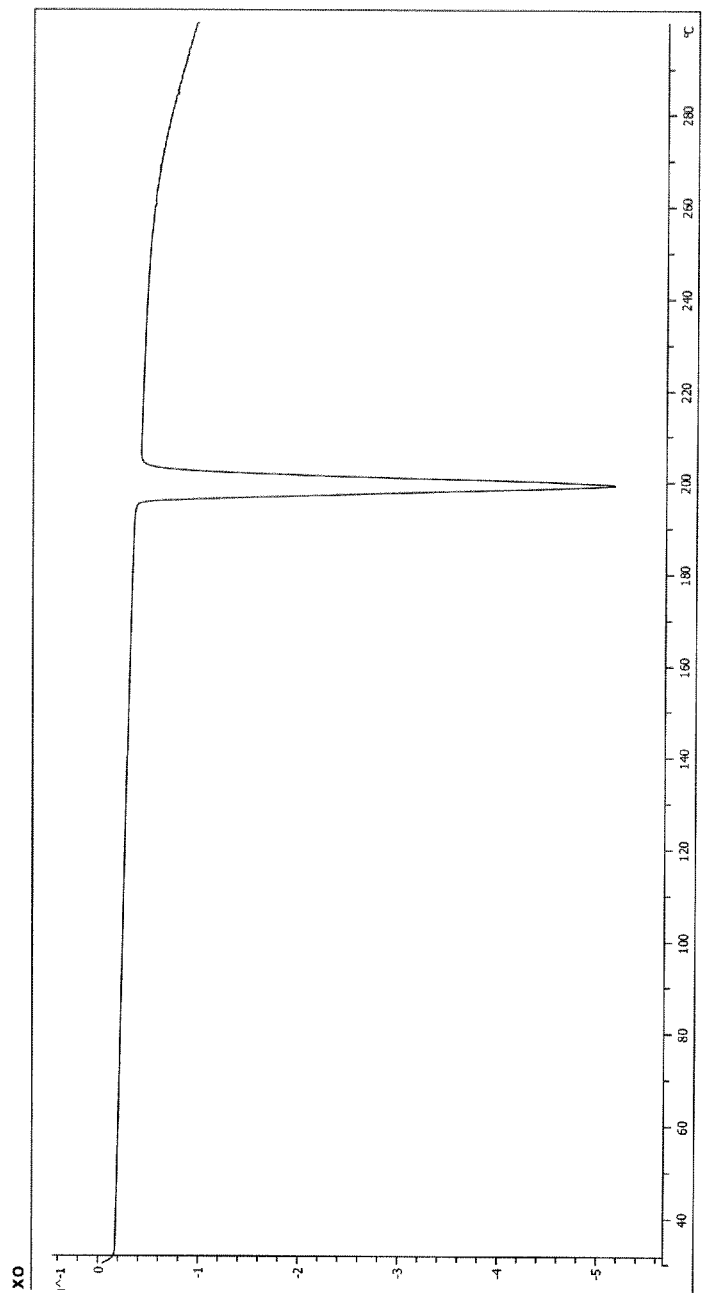
FIG. 2 shows a characteristic DSC thermogram of crystalline Pridopidine hydrobromide.

Following this procedure the DSC thermogram shown in FIG. 2 was obtained. FIG. 2 shows an endotherm with an onset of about 196° C., as obtained with DSC.

Thermo Gravimetric Analysis

Thermo gravimetric analysis (TGA) experiments were conducted on a Mettler Toledo TGA/SDTA 851e. The sample (approx. 10 mg) was heated in an open Al crucible from 30° C. to 300° C. at 10° C./min. The TGA was continuously purged with dry nitrogen, and was routinely calibrated with Indium and aluminum. Data was evaluated using Mettler-Toledo StarE ver. 9.2 software package.

Figure 4:
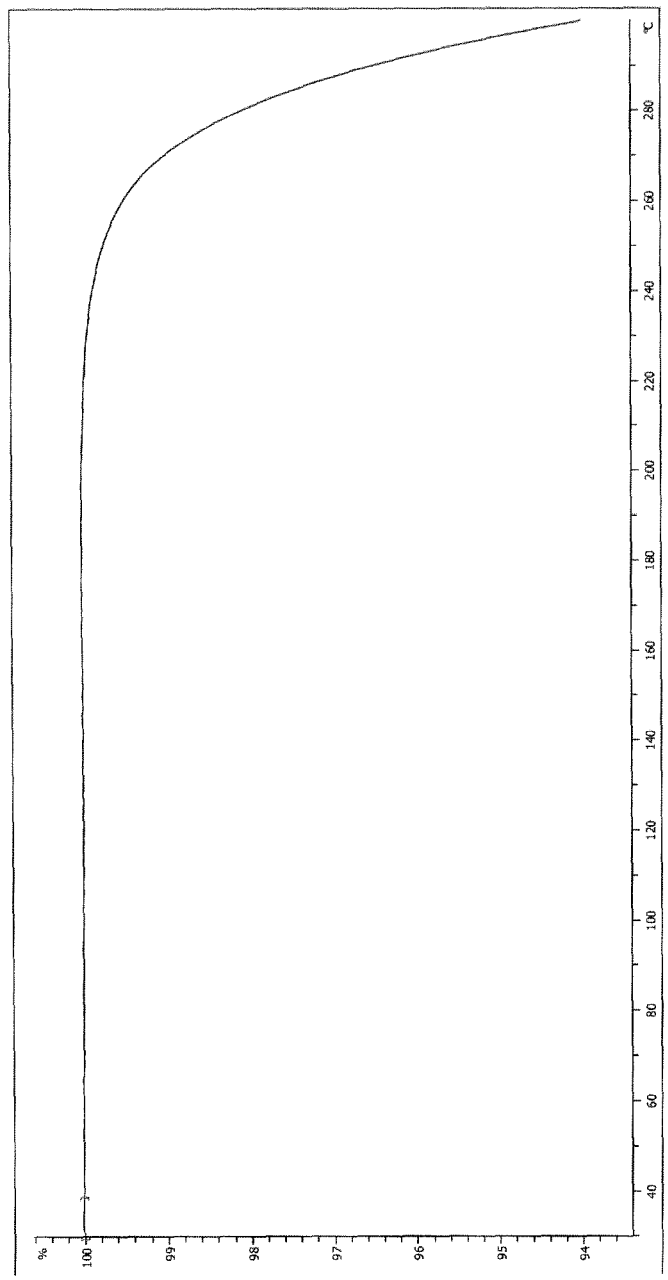
FIG. 4 shows a characteristic TGA thermogram of crystalline Pridopidine hydrobromide.

Following this procedure the TGA thermogram shown in FIG. 4 was obtained. The TGA thermogram in FIG. 4 shows a minor loss of mass below 130° C., a minor loss of mass at approximately 140° C. and 180° C. and a major loss of mass above approximately 230° C.

Fourier Transform Infrared Spectroscopy

Fourier Transform infrared spectroscopy (FTIR) experiments were conducted on a Perkin-Elmer Spectrum One FTIR instrument equipped with an attenuated total reflection (ATR) unit Goldengate supplied from Specac. The system was controlled using Spectrum Ver. 5.0.1 software. The samples (approx. 1-2 mg) were placed directly on the diamond surface of the ATR unit and the anvil pressed firmly against the sample. Samples were analysed in the wave number region 4000-600 cm-1. The instrument was routinely calibrated against internal polystyrene filters.

Figure 3:
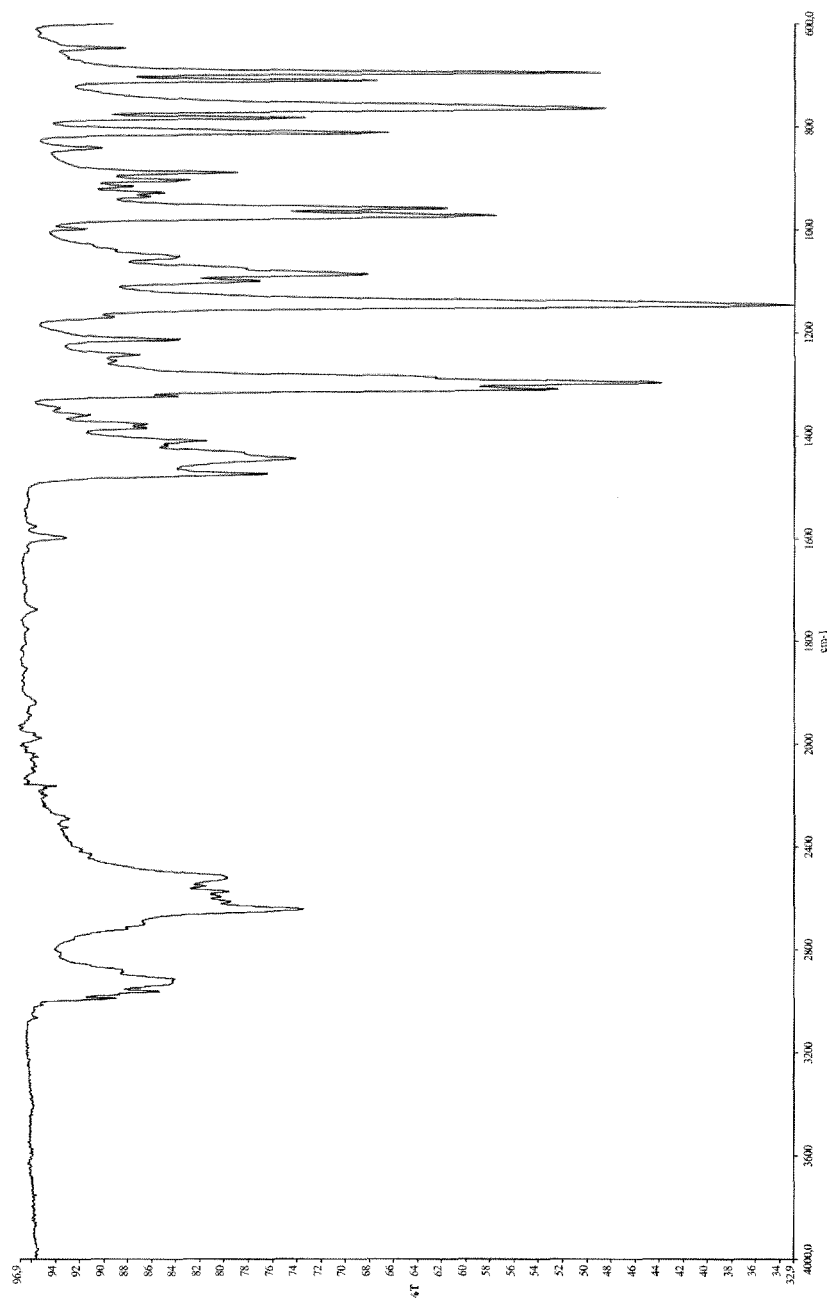
FIG. 3 shows a characteristic FT-IR spectrum of crystalline Pridopidine hydrobromide.

Following this procedure the FT-IR spectrum of crystalline pridopidine hydrobromide shown in FIG. 3 was obtained. The IR spectrum in FIG. 3 has absorptions at about 2950 cm$^{-1}$, 2700-2500 cm$^{-1}$, 1550 cm$^{-1}$, 1450 cm$^{-1}$, 1300 cm$^{-1}$, 1150 cm$^{-1}$, 1100 cm$^{-1}$, 950 cm$^{-1}$, 900 cm$^{-1}$, 850 cm$^{-1}$, 750 cm$^{-1}$, and 650 cm$^{-1}$.

Karl Fischer Titration

Water determinations using Karl Fischer (KF) titrations were performed using Metrohm KF 756 KF Coulometer equipped with a generator electrode without diaphragm. The titrator was equipped with a Metrohm 832 KF Thermoprep oven. The sample was weighed off in small HPLC glass vials, sealed and introduced into the oven (130° C.). Here a needle was used to puncture the rubber septum of the HPLC vial and a dry carrier gas (N2) was used to carry the released water via heated tubing to the titration chamber.

Prior to sample titration, a series of blanks were titrated to determine the blank level. Results were automatically corrected for the blank value. The instrument was routinely controlled by using solid standards with certified water content.

Dynamic Vapour Sorption Measurements

Dynamic vapour sorption (DVS) measurements were conducted using a Q5000 SA from TA instruments.

Experiments were conducted in two sorption/desorption cycles between 0% RH and 95% RH. Prior to the first sorption cycle the sample was equilibrated at 20% RH and the initial weight recorded. Samples were analyzed in an aluminium pan. Humidity was brought down to 0% RH and the sample dried until the weight had stabilized within a given limit. The temperature was held constant at 25° C. Maximum step time was 720 min. Gas flow was 200 cm$^3$/min.

Figure 5:
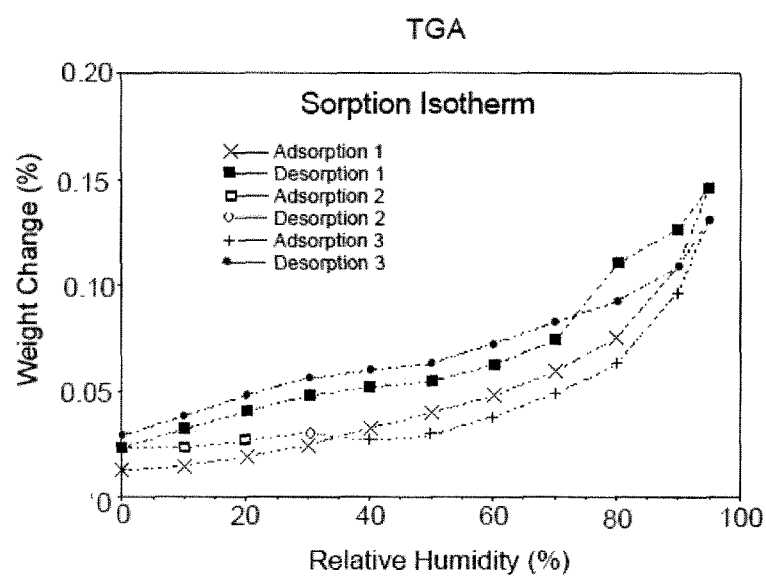
FIG. 5 shows a characteristic dynamic vapour sorption (DVS) profile of crystalline Pridopidine hydrobromide in the relative humidity range 0-95%. Size 8.6650 mg, Method adsorption 0-95% 2 cycles 25. Instrument TGA Q5000 V3.10 Build 258.
Figure 6:
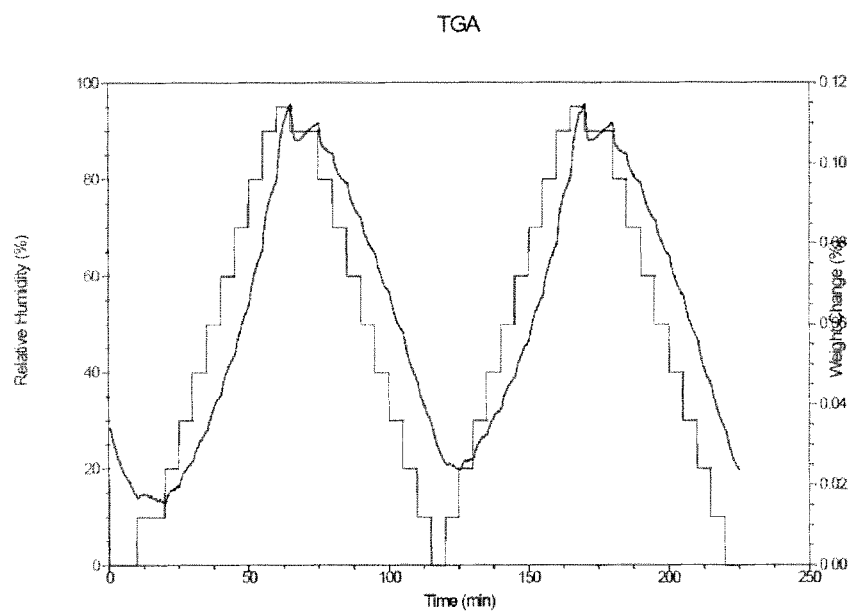
FIG. 6 shows a characteristic dynamic vapour sorption (DVS) moisture sorption and desorption kinetics plot of crystalline pridopidine hydrobromide in the relative humidity range 0-95%. Size 11.4530 mg, Method adsorption 0-95% 2 cycles 25. Instrument TGA Q5000 V3.5 Build 252.
Figure 7:
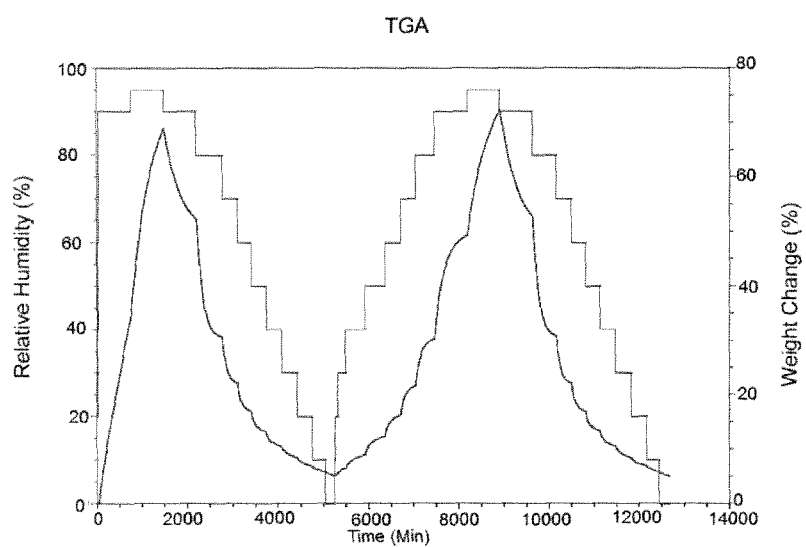
FIG. 7 shows a characteristic dynamic vapour sorption (DVS) moisture sorption and desorption kinetics plot of crystalline pridopidine hydrochloride in the relative humidity range 0-95%. Size 9.9530 mg, Method adsorption 0-95% 2 cycles 25. Instrument TGA Q5000 V3.5 Build 252.
Figure 8:
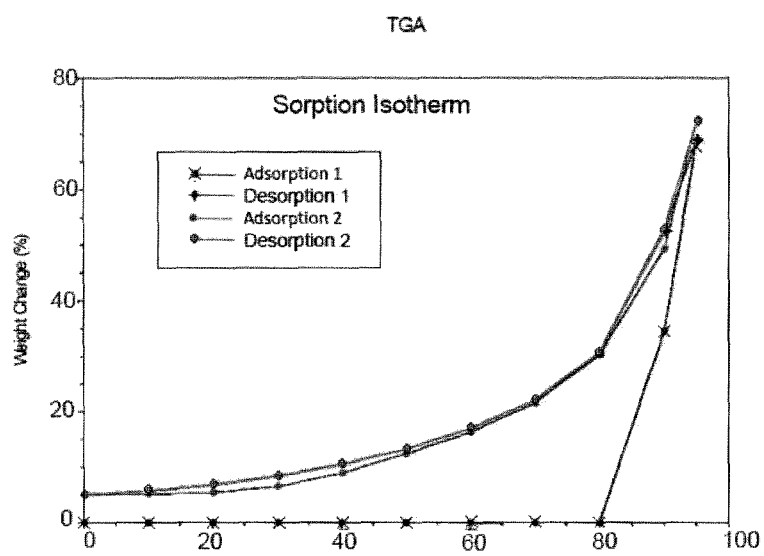
FIG. 8 shows a characteristic dynamic vapour sorption (DVS) profile of crystalline pridopidine hydrochloride in the relative humidity range 0-95%. 11.4530 mg, Method adsorption 0-95% 2 cycles 25. Instrument TGA Q5000 V3.5 Build 252.
Figure 9:
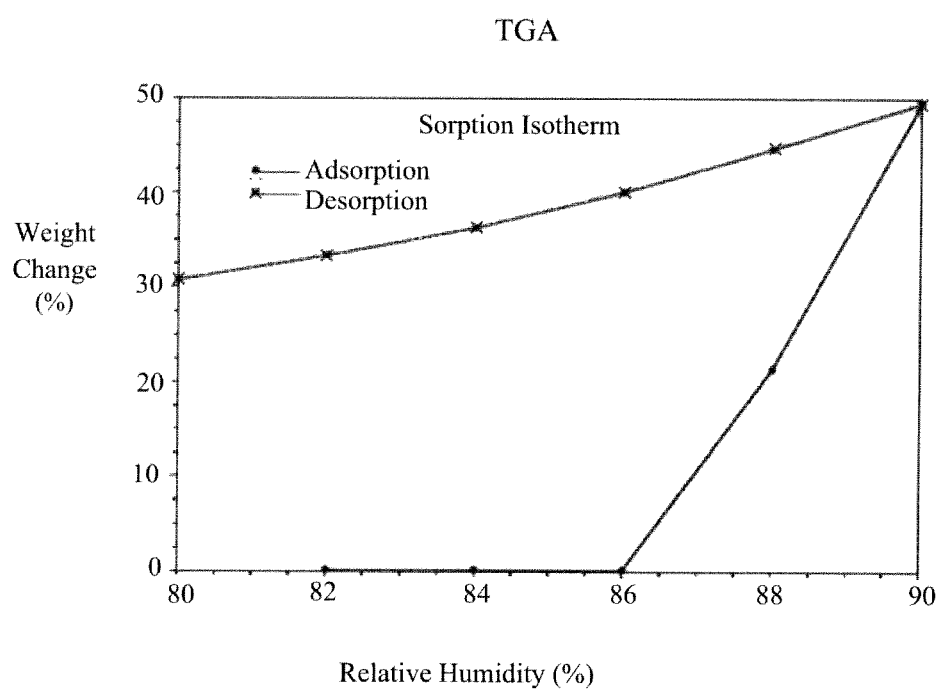
FIG. 9 shows a characteristic dynamic vapour sorption (DVS) isotherm with smaller steps in the mid eighties relative humidity range for crystalline pridopidine hydrochloride in the relative humidity range 0-95%. 5.7650 mg, Method adsorption 80-90-80%. Instrument TGA Q5000 V3.5 Build 252.

Following this procedure the DVS profile shown in FIG. 5 was obtained. The DVS profile in FIG. 5 has a dynamic vapour sorption (DVS) profile which shows that between 0 and 95% relative humidity, the salt gradually gained approximately 0.15% weight, which is lost during desorption.

CHN Measurements

CHN measurements were performed at Mikroanalytisk Laboratorium, Kemisk Institut, University of Copenhagen, using a Flash EA 1112 analyzer.

Approximately two milligrams of compound was weighed into a small tin beaker and inserted into the combustion chamber. The resulting gasses were collected on a column and analyzed via gas chromatography. Analyses were performed in duplicate.

The invention claimed is:

1. A hydrobromide salt of 4-(3-methanesulfonyl-phenyl)-1-propyl-piperidine (Pridopidine) having an X-ray powder diffraction pattern with reflections corresponding to at least the following d-spacing values: 10.8, 7.6, 6.9, 6.0, 5.7, 5.4, 5.3, 5.2, 4.7, 4.6, 4.3, 4.2, 4.0, 3.8, 3.7, 3.6, 3.5, 3.4, 3.3, 3.2, 3.1.

2. The hydrobromide salt of claim 1 provided in an anhydrous form and non-solvated form.

3. The hydrobromide salt of claim 1 provided in an anhydrous form which is in a substantially crystalline form.

4. The hydrobromide salt of claim 1 characterized by having an IR spectrum with absorptions at about 2950 cm$^{-1}$, 2700-2500 cm$^{-1}$, 1550 cm$^{-1}$, 1450 cm$^{-1}$, 1300 cm$^{-1}$, 1150 cm$^{-1}$, 1100 cm$^{-1}$, 950 cm$^{-1}$, 900 cm$^{-1}$, 850 cm$^{-1}$, 750 cm$^{-1}$, and 650 cm$^{-1}$.

5. A pharmaceutical composition comprising a therapeutically effective amount of the hydrobromide salt according to claim 1, together with one or more adjuvants, excipients, carriers and/or diluents.

6. The pharmaceutical composition of claim 5, wherein the therapeutically effective amount of 4-(3-methanesulfonyl-phenyl)-1-propyl-piperidine (Pridopidine) is from 1 mg to 500 mg.

7. The pharmaceutical composition of claim 5, wherein the therapeutically effective amount of 4-(3-methanesulfonyl-phenyl)-1-propyl-piperidine (Pridopidine) is from 10 mg to 100 mg.

8. The pharmaceutical composition of claim 5, wherein the therapeutically effective amount of 4-(3-methanesulfonyl-phenyl)-1-propyl-piperidine (Pridopidine) is 45 mg.

9. The pharmaceutical composition of claim 5, wherein the therapeutically effective amount of 4-(3-methanesulfonyl-phenyl)-1-propyl-piperidine (Pridopidine) is 67.5 mg.

10. A method of treatment, prevention or alleviation of a dopamine mediated disorder of a living animal body, including a human, which method comprises the step of administering to such a living animal body in need thereof, a therapeutically effective amount of the hydrobromide salt according to claim 1.

11. A method for treating a subject in need of treatment for Huntington's disease which comprises administering to the subject a therapeutically effective amount of the hydrobromide salt according to claim 1, thereby treating the subject.

12. The method of claim 11, wherein the amount of 4-(3-methanesulfonyl-phenyl)-1-propyl-piperidine (Pridopidine) administered is from 1 mg to 500 mg 1 to 4 times per day.

13. The method of claim 11, wherein the amount of 4-(3-methanesulfonyl-phenyl)-1-propyl-piperidine (Pridopidine) administered is from 10 mg to 150 mg 1 to 4 times per day.

14. The method of claim 11, wherein the amount of 4-(3-methanesulfonyl-phenyl)-1-propyl-piperidine (Pridopidine) administered is 45 mg twice per day.

15. The method of claim 11, wherein the amount of 4-(3-methanesulfonyl-phenyl)-1-propyl-piperidine (Pridopidine) administered is 67.5 mg twice per day.

16. The hydrobromide salt of claim 1 provided in an anhydrous form.

17. The hydrobromide salt of claim 1, wherein the hydrobromide salt is non-hygroscopic between 0% and 95% relative humidity.

* * * * *